United States Patent [19]

Hanifl et al.

[11] Patent Number: 4,863,057

[45] Date of Patent: Sep. 5, 1989

[54] DUAL LOCKED CONTAINER SYSTEM

[75] Inventors: Paul H. Hanifl, Barrington; John J. Newton, Jr., Palatine, both of Ill.; Donald J. Mosior, Lake Geneva, Wis.

[73] Assignee: Sage Products, Inc., Cary, Ill.

[21] Appl. No.: 188,025

[22] Filed: Apr. 29, 1988

[51] Int. Cl.⁴ ............................................ B65D 21/02
[52] U.S. Cl. ............................... 220/23.83; 220/23.4; 220/18; 206/465; 206/468; 312/109
[58] Field of Search .............. 220/4 C, 4 A, 18, 23.4, 220/23.83, 23.86, 23.6; 206/464, 465, 468, 501; 312/109, 107; 221/46, 197, 154, 287

[56] References Cited

U.S. PATENT DOCUMENTS 2,746,457 9/1954 Musacchia ........................ 220/22.5
4,771,907 9/1988 Torney ............................. 220/23.83

Primary Examiner—Stephen Marcus
Assistant Examiner—Gilbert W. Reece
Attorney, Agent, or Firm—Lee & Smith

[57] ABSTRACT

A secure container system comprising a first container with a second container mounted thereon, the container having adjacent sides that are complementary to one another. The first container includes a pair of spaced channels and the second channel includes opposite flanges which engage the channels for mounting the second container on the first. The first container has a door which, when closed, includes an extended portion comprising a stop for selectively preventing lateral movement of the second container relative to the first. When the door is opened, the second container may be laterally removed from its mounting on the first container.

17 Claims, 1 Drawing Sheet

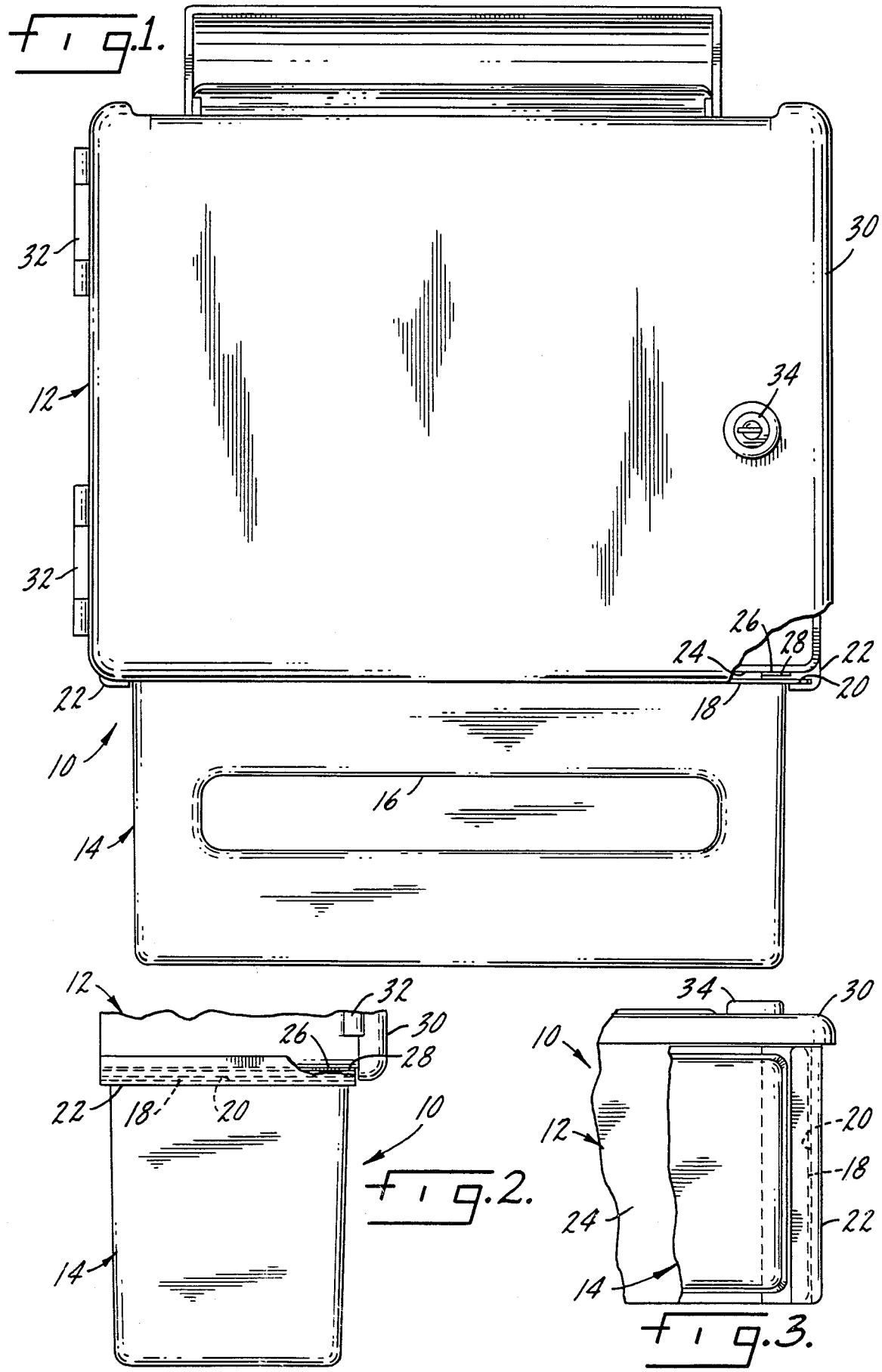

4,863,057

DUAL LOCKED CONTAINER SYSTEM

BACKGROUND OF THE INVENTION

This invention relates to multiple container systems, and in particular to a container system having a second container removably mounted on a first container, with the first container being provided with means for temporarily locking the second container to the first.

Sterility and cleanliness are constant concerns in a hospital. As a result, disposble, one-time use products have proliferated to the extent that their proper dissemination and disposal have become major concerns of hospitals. Typically, disposable products, such as sharps, tissues and gloves are stored on shelves or in cabinets, and disposed of in waste baskets or other portable containers which are strategically placed within the hospital room. Dispensing and disposal of such products in secure containers has received little consideration.

SUMMARY OF THE INVENTION

The invention relates to a secure container system intended to be mounted on the wall in a room within a hospital, clinic or medical office. It is composed to two containers, the second of which is mounted on the first such that the second can be laterally removed from the first when desired. A stop is provided on the first container for selectively preventing removal of the second container, the stop being positionable in a first orientation to lock the second container in place and in a second orientation to unlock the second container to permit its removal.

For mounting of the second container on the first, the second container includes opposite flanges extending outwardly from opposite edges of the container. A pair of spaced, parallel channels are located on the first container, with each of the channels being shaped and located to accommodate one of the flanges of the second container. In accordance with the preferred embodiment of the invention, each channel is formed in a bracket which is either an integral portion of the first container, or adhesively secured thereto.

The first container includes a door oriented generally perpendicular to the mounting location of the second container on the first. The door has an extended portion projecting adjacent the mounting location, with that extended portion comprising the stop that may selectively prevent or permit removal of the second container from the first. The door is provided with a lock so that when the door is closed and latched, the two containers are irremovably secured together.

In accordance with the preferred embodiment of the invention, the first container comprises a cabinet for disposal of sharps, gloves, and other similar litter. The second container is slotted for dispensing of surgical gloves which, when used, may be disposed of in the first container.

BRIEF DESCRIPTION OF THE DRAWINGS

The invention is described in greater detail in the following description of an example embodying the best mode of the invention taken in conjunction with the drawing figures, in which:

FIG. 1 is a front elevational view of the container system according to the invention with a portion of the first container broken away to illustrate detail, FIG. 2 is a side elevational view of the two containers, with the majority of the first container removed as superfluous, and again with a portion broken away to illustrate detail, and FIG. 3 is a partial bottom plan view of the right hand portion of the container system of FIG. 1, again with portions broken away to illustrate detail.

DESCRIPTION OF AN EXAMPLE EMBODYING THE BEST MODE OF THE INVENTION

The container system according too the invention is illustrated generally at 10 in the drawing figures. It is composed of two containers, a first container 12 and a second container 14. As illustrated and described in greater detail below, the second container 14 is mounted on the bottom of the first container 12 and may be laterally removed from the container 12 when desired.

The first container 12 is the outer enclosure for a wall-mounted sharps disposal system, as disclosed and described in U.S. Pat. No. 4,715,498, issued Dec. 29, 1987, the disclosure of which is incorporated herein by reference. As set forth in said patent, the container 12 is inteded to include a second, inner disposable container which, when filled with discarded sharps and other wastes, may be removed from the container 12 and suitably disposed of.

The second container 14 has an opening dispensing slot 16 so that any items contained within the container 14 can be readily dispensed. The container 14 is sized appropriately in the illustrated embodiment of the invention to accommodate a box of disposable gloves (not illustrated) which is installed within the container 14 with its own dispensing slot in alignment with the dispensing slot 16. When the supply of gloves within the box is exhausted, the second container 14 is removed from the first container 12, the empty box discarded and a new box substituted in its place. It should be evident that the container 14 may be used for selective distribution of other items, such as tissues, as well.

The second container 14 includes a pair of opposite flanges 18 extending outwardly from opposite edges of the second container 14. One of the flanges 18 at one edge of the container 14 is illustrated in FIGS. 1 and 3, it being evident that the opposite flange on the opposite edge of the container is identical, extending in the opposite direction. Each of the flanges 18 is engaged within a channel 20 of a bracket 22, the brackets 22 being secured to opposite sides of the bottom of the first container 12. Each bracket 22 may be an integral portion of the container 12 or, as shown in the illustrated embodiment, each of the brackets 22 may be adhesively secured to the bottom 24 of the container 12 by means of an adhesive strip 26 located within a longitudinal groove 28 extending the length of each of the brackets 22.

The container 12 has a front door 30 which is mounted on the container 12 by a pair of hinges 32. When closed in the orientation illustrated in the drawing figures, the door 30 extends beneath the bottom 24 to block removal of the container 14 from the container 12. The door 30 therefore acts as a stop when closed. When the door 30 is opened, the container 14 may readily be laterally removed from the brackets 22.

The container 12 includes a lock 34 in the door 30 for securing the door 30 in the closed orientation. The single lock 34 therefore serves to protect both the contents of the first container 12 and also to prevent removal of the second container 14 by preventing opening of the door 30. As illustrated, the bottom 24 of the container 12 is generally flat, and the top of the container 14 is generally complementary to that configuration so that the two containers 12 and 14 may be joined without interference. The top of the container 14 may be open, as illustrated in co-pending U.S. Design Patent application Ser. No. 182307, filed 4/15/88, entitled "Glove Dispenser", or may be closed, depending on the intended usage of the container 14. The door 30 is generally perpendicular to the juncture of the two containers 12 and 14 in order to provide the necessary inhibiting stop when the door 30 is closed.

Various changes can be made to the invention without departing from the spirit thereof or scope of the following claims.

What is claimed is:

1. A secure container system for mounting on a wall, comprising
   a. a first container including a side having a predetermined exterior configuration,
   b. a second container including a side having an exterior configuration complementary to said predetermined configuration,
   c. means mounting said second container on the exterior of said first container with said sides adjacent one another and with said second container being accessible independent of said first container, said mounting means being formed to permit lateral movement of said second container relative to said first container, and
   d. stop means mounted on said first container for selectively preventing lateral movement of said second container relative to said first container, said stop means having an extended portion projecting adjacent a portion of said second container and being positionable in a first orientation to lock said second container to prevent such lateral movement and a second orientation to unlock said second container to permit such lateral movement.

2. A container system according to claim 1 in which said mounting means comprises opposite flanges extending outwardly from opposite edges of said side of said second container, and a pair of spaced, parallel channels located on said side of said first container, each of said channels being shaped to accommodate one of said flanges.

3. A container system according to claim 2 in which each channel is formed in a bracket secured to said side of said first container.

4. A container system according to claim 3 in which said bracket is adhesively secured to said side of said first container.

5. A container system according to claim 1 in which said sides are generally flat.

6. A container system according to claim 1 in which said first container includes a door oriented generally perpendicular to said side of said first container, and said door has an extended portion projecting adjacent said mounting means, said extended portion comprising said stop means.

7. A container system according to claim 6 in which said door includes hinges securing said door to said first container, and including a latch for said door.

8. A container system according to claim 7 in which said side of said first container is generally flat and lies in a first plane, and said hinges lie in a second plane normal to said first plane.

9. A secure container system for mounting on a wall, comprising
   a. a first container including a generally flat exterior side,
   b. a second container including an exterior side having a configuration complementary to said flat side,
   c. means mounting said second container on the exterior of said first container with said sides adjacent one another and with said second container being accessible independent of said first container, said mounting means being formed to permit lateral movement of said second container relative to said first container, and
   d. a door secured to said first container and oriented generally perpendicular to said flat side, said door having an extended portion projecting adjacent said mounting means when said door is closed, said extended portion comprising a stop for selectively preventing lateral movement of said second container relative to said first container when said door is closed.

10. A container system according to claim 9 in which said mounting means comprises opposite flanges extending outwardly from opposite edges of said side of said second container, and a pair of spaced, parallel channels located on said side of said first container, each of said channels being shaped to accommodate one of said flanges.

11. A container system according to claim 10 in which each channel is formed in a bracket secured to said side of said first container.

12. A container system according to claim 11 in which said bracket is adhesively secured to said side of said first container.

13. A container system according to claim 9 in which said door includes hinges securing said door to said first container, and including a latch for said door.

14. A container system according to claim 13 in which said flat side lies in a first plane and said hinge lies in a second plane normal to said first plane.

15. A secure container system for mounting on a wall comprising
   a. a first container including a flat exterior side having spaced, parallel channels located thereon,
   b. a second container having opposite flanges extending outwardly from opposite edges of one exterior side of said second container, said flanges being complementary to and engaging a respective one of said channels such that said second container may be moved laterally relative to said first container, said channels and said flanges comprising a means for mounting said second container on said first container with said second container being accessible independent of said first container, and
   c. a door secured to said first container and oriented generally perpendicular to said flat side, said door having an extended portion projecting adjacent said mounting means when said door is closed, said extended portion comprising a stop for selectively preventing lateral movement of said second container relative to said first container when said door is closed.

16. A container system according to claim 15 in which said channel is formed in a bracket secured to said side of said first container.

17. A container system according to claim 16 in which said bracket is adhesively secured to said side of said first container.

* * * * *